United States Patent [19]
Caulkett et al.

[11] Patent Number: 4,999,377

[45] Date of Patent: Mar. 12, 1991

[54] CHEMICAL COMPOUNDS

[75] Inventors: Peter W. R. Caulkett, Macclesfield; Michael J. Cooper, Congleton; Murdoch Eakin; Geraint Jones, both of Macclesfield, all of England

[73] Assignee: Imperial Chemical Industries PLC, London, England

[21] Appl. No.: 298,752

[22] Filed: Jan. 19, 1989

[30] Foreign Application Priority Data

Jan. 21, 1988 [GB] United Kingdom ............... 8801306

[51] Int. Cl.$^5$ .................. A61K 31/275; A61K 31/16; C07C 255/50; C07C 233/05
[52] U.S. Cl. ................................. 514/507; 514/522; 514/575; 514/614; 514/616; 514/620; 558/414; 560/312; 562/621; 564/157; 564/162; 564/165; 424/468
[58] Field of Search ...................... 564/157, 162, 165; 514/620, 614, 616, 507, 575, 522; 562/621; 560/312

[56] References Cited

U.S. PATENT DOCUMENTS

| | | | |
|---|---|---|---|
| 4,329,358 | 5/1982 | Ainsworth et al. | 564/165 |
| 4,727,067 | 2/1988 | Ostermayer et al. | 564/165 |
| 4,772,631 | 9/1988 | Holloway et al. | 564/165 |

FOREIGN PATENT DOCUMENTS 0254532 1/1988 European Pat. Off. ............ 564/165

*Primary Examiner*—Joseph Paul Brust
*Assistant Examiner*—Jacqueline Haley
*Attorney, Agent, or Firm*—Cushman, Darby & Cushman

[57] ABSTRACT

2-(2-Hydroxy-3-phenoxypropylamino)ethylphenoxyacetamide compounds are disclosed as useful in the treatment of obesity and related conditions. Processes for their preparation are described, as are novel intermediates and pharmaceutical compositions containing them.

12 Claims, No Drawings

CHEMICAL COMPOUNDS

The present invention relates to 2-(2-hydroxy-3-phenoxypropylamino)ethylphenoxymethyl compounds and in particular to such compounds containing an amido group. This invention further relates to processes and intermediates for their preparation, to their use in methods of therapy and to pharmaceutical compositions containing them. Administration of the compounds of this invention to warm-blooded animals provides a thermogenic effect, that is thermogenesis is stimulated and administration of the compounds is of use, for example, in the treatment of obesity and related conditions such as obesity of mature onset diabetes.

In EP-A-140243 there is described a series of phenoxyacetic acid derivatives which are said to be of value in treating obesity. We have now discovered that, unexpectedly, the amides of the present invention provide significant thermogenic properties at doses which cause relatively little cardiac stimulation and/or other side-effects. It is understood that selectivity of thermogenic effect is an important requirement for a useful therapeutic agent in the treatment of, for example, obesity and related conditions.

It will be understood, also, that a further important requirement for a useful therapeutic agent is to be capable of being sufficiently bioavailable, particularly after oral administration. The compounds of the present invention show advantages in that they provide suitable duration of action; in particular, following oral administration in an appropriate pharmaceutical formulation, the compounds show stability in the gut (from which they are absorbed into the bloodstream) allowing higher levels of compounds in the bloodstream. Clearly the more suitable the bioavailability and/or duration of action the lower the need to administer frequent doses and the lower the possibility of undesirable side-effects Accordingly the present invention provides a compound of the formula (I):

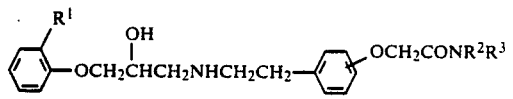

(I)

wherein
$R^1$ is hydrogen, fluoro or chloro;
$R^2$ is hydrogen, $C_{1-6}$ alkyl or $C_{3-6}$ alkenyl either group being optionally substituted by hydroxy, $C_{1-4}$ alkoxy, phenoxy, carbamoyl, $C_{1-6}$ alkylcarbamoyl, di-$C_{1-6}$ alkylcarbamoyl, pyridyl, phenyl or chlorophenyl, or $R^2$ is $C_{3-6}$ alkynyl, $C_{3-5}$ cycloalkyl or is phenyl optionally substituted by halo, $C_{1-4}$ alkyl, $C_{1-4}$ alkoxy, trifluoromethyl, cyano or nitro;
$R^3$ is hydrogen, $C_{1-6}$ alkyl or a group —$OR^4$ wherein $R^4$ is hydrogen, $C_{1-6}$ alkyl optionally substituted by hydroxy or $C_{1-4}$ alkoxy, $C_{3-6}$ alkenyl optionally substituted by hydroxy or $C_{1-4}$ alkoxy, or $R^4$ is $C_{3-6}$ alkynyl, phenyl, naphthyl, phenyl $C_{1-4}$ alkyl or naphthyl $C_{1-4}$ alkyl;
or $R^2$ and $R^3$ together form a $C_{4-7}$ methylene chain (wherein one methylene unit may optionally be replaced by oxygen or sulphur situated at least two carbon atoms distant from the nitrogen atom of —$NR^2R^3$) in which two adjacent methylene units may optionally be replaced by two carbon atoms of a benzene ring fused to said $C_{4-7}$ methylene chain said benzene ring optionally substituted by halo, $C_{1-4}$ alkyl, $C_{1-4}$ alkoxy, trifluoromethyl, cyano or nitro, or $R^2$ and $R^4$ together form a $C_{3-4}$ methylene chain : or a pharmaceutically acceptable salt thereof.

In one aspect $R^1$ and $R^3$ are as above defined and $R^2$ is hydrogen, $C_{1-6}$ alkyl or $C_{3-6}$ alkenyl either group being optionally substituted by hydroxy, $C_{1-4}$ alkoxy, phenoxy, carbamoyl, phenyl or chlorophenyl, or $R^2$ is $C_{3-6}$ alkynyl, $C_{3-5}$ cycloalkyl or is phenyl optionally substituted by halo, $C_{1-4}$ alkyl, $C_{1-4}$ alkoxy, trifluoromethyl, cyano or nitro, or $R^2$ is joined to $R^3$ or $R^4$ as hereinabove defined $R^1$ is hydrogen, chloro or fluoro. Preferably $R^1$ is hydrogen.

The —$OCH_2CONR^2R^3$ substituent in the compounds of the formula (I) is generally situated in the meta or para position of the phenyl ring relative to the phenoxypropylaminoethyl substituent. Preferably the substituents are in a para relationship.

In another aspect $R^2$ is $C_{1-6}$ alkyl for example methyl, ethyl, isopropyl, n-propyl, butyl, pentyl and hexyl or is $C_{3-6}$ alkenyl for example allyl. Optional substituents for $R^2$ being $C_{1-6}$ alkyl or $C_{3-6}$ alkenyl include hydroxy, $C_{1-4}$ alkoxy for example methoxy or ethoxy and phenyl Further optional substituents for $R^2$ being $C_{1-6}$ alkyl or $C_{3-6}$ alkenyl include carbamoyl, $C_{1-6}$ alkylcarbamoyl for example methylcarbamoyl, di-$C_{1-6}$alkylcarbamoyl for example dimethylcarbamoyl and pyridyl.

An example of $R^2$ being $C_{3-6}$ alkynyl is propynyl.

$R^2$ can also be $C_{3-5}$ cycloalkyl for example cyclopropyl, cyclobutyl and cyclopentyl.

When $R^2$ is phenyl optional substituents are halo for example bromo, chloro and fluoro, $C_{1-4}$ alkyl for example methyl and ethyl, $C_{1-4}$ alkoxy for example methoxy and ethoxy, trifluoromethyl, cyano and nitro.

In one aspect $R^3$ is hydrogen or $C_{1-6}$ alkyl for example methyl or ethyl.

In a further aspect $R^3$ is a group —$OR^4$, thus forming a hydroxamic acid or derivative thereof, preferably $R^4$ is hydrogen, $C_{1-6}$ alkyl optionally substituted by hydroxy or $C_{1-4}$ alkoxy for example methyl, ethyl, propyl, butyl, 2-hydroxyethyl, 3-hydroxypropyl, 2-methoxyethyl or 2-ethoxyethyl, or $R^4$ is $C_{3-6}$ alkenyl optionally substituted by hydroxy or $C_{1-4}$ alkoxy for example allyl, or $C_{3-6}$ alkynyl for example propynyl In particular $R^4$ is hydrogen or $C_{1-6}$ alkyl.

In yet a further aspect $R^2$ and $R^3$ together form a $C_{4-7}$ methylene chain, so as to form, together with the nitrogen atom to which they are attached, a 5–8 membered heterocyclic ring. Optionally one methylene unit of the chain is replaced by oxygen or sulphur. For example —$NR^2R^3$ may represent pyrrolidino, piperidino, hexahydroazepino, morpholino or thiamorpholino. Any two adjacent methylene units of the chain may optionally be replaced by two carbon atoms of a benzene ring fused to said chain and said benzene ring may be optionally substituted by halo for example chloro, fluoro or bromo; $C_{1-4}$ alkyl for example methyl, ethyl or propyl; $C_{1-4}$ alkoxy for example methoxy or ethoxy; trifluoromethyl, cyano or nitro.

In another aspect $R^2$ and $R^4$ together form a $C_{3-4}$ methylene chain, so that together with the -N-O- atoms the isooxazolidino or tetrahydroisooxazino moiety is formed.

A preferred group of compounds of the present invention comprises those compounds of the formula (I) wherein $R^1$ is hydrogen; the phenoxypropylaminoethyl and —OCH$_2$CONR$^2$R$^3$ substituents are in para-relationship; and —NR$^2$R$^3$ is C$_{1-6}$ alkylamino optionally substituted by C$_{1-4}$ alkoxy or carbamoyl; di-C$_{1-6}$ alkylamino, piperidino or morpholino.

A particularly preferred group of compounds of the present invention comprises those compounds of the formula (I) wherein R$^1$ is hydrogen; the phenoxypropylaminoethyl and —OCH$_2$CONR$^2$R$^3$ substituents are in para-relationship; and —NR$^2$R$^3$ is methylamino, ethylamino, dimethylamino, diethylamino, 3-methoxypropylamino, 3-ethoxypropylamino, 2-methoxyethylamino, 2-ethoxyethylamino, methylethylamino and piperidino.

We believe, but do not wish to be bound by theory, that the compounds of the formula (I), at least in part, when administered to a warm-blooded animal form compounds of the formula (I) wherein the —CONR$^2$R$^3$ group is replaced by a —COOH group. Such compounds possess significant thermogenic properties with selectivity of effect. These compounds are novel and can be administered to a warm-blooded animal in an appropriate pharmaceutical composition but preferably are formed in vivo from the compounds of the formula (I).

Thus in another aspect the present invention provides the compounds of the formula (II)

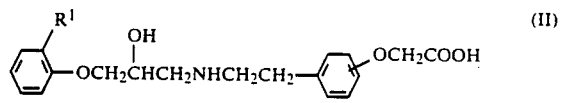

(II)

wherein R$^1$ is hydrogen, chloro or fluoro; and pharmaceutically acceptable salts thereof.

Preferably R$^1$ is hydrogen and the phenoxypropylaminoethyl and —OCH$_2$COOH substituents are in para-relationship.

The compounds of the formula (I) are basic and may be isolated and used either in the form of the free base or of a pharmaceutically acceptable acid-addition salt thereof. In addition, the compounds of the formula (II) are amphoteric and may be used in the zwitterionic form, or as a pharmaceutically acceptable acid addition salt, or as a salt with a base affording a pharmaceutically acceptable cation. Particular examples of pharmaceutically acceptable acid-addition salts include, for example, salts with inorganic acids such as hydrohalides (especially hydrochlorides or hydrobromides), sulphates and phosphates, and salts with organic acids such as succinates, citrates, lactates, tartrates, oxalates and salts derived from acidic water-soluble polymers. Particular examples of salts with bases affording a pharmaceutically acceptable cation include, for example, alkali metal and alkaline earth metal salts, such as sodium, potassium, calcium and magnesium salts, and ammonium salts and salts with suitable organic bases such as triethanolamine.

It will be appreciated that the compounds of formula I contain one or more asymmetric carbon atoms (and the compounds of formula (II) contain one asymmetric carbon atom) and can exist as optically active enantiomers or as optically inactive racemates. The present invention encompasses any enantiomer, racemate and/or (when two or more asymmetric carbon atoms are present) diastereoisomer, which when administered in a therapeutic amount provides a thermogenic effect in warm-blooded animals, it being well known in the chemical art how to prepare individual enantiomers, for example by resolution of the racemate or by stereospecific synthesis, and how to determine the thermogenic properties, for example, using the standard tests described hereinafter. It is preferred that the compounds of the present invention are provided in the laevorotatory optically active form (-) which corresponds to (S) absolute configuration under the Cahn-Prelog-Ingold rules.

In order to use a compound of the present invention or a pharmaceutically acceptable salt thereof for the therapeutic treatment of warm-blooded mammals including humans, in particular for treating obesity, it is normally formulated in accordance with standard pharmaceutical practice as a pharmaceutical composition.

Therefore in another aspect the present invention provides a pharmaceutical composition which comprises a compound of the formulae (I) or (II) or a pharmaceutically acceptable salt thereof and a pharmaceutically acceptable carrier.

The pharmaceutical compositions of this invention may be administered in standard manner for example by oral or parenteral administration. For these purposes they may be formulated by means known to the art into the form of, for example, tablets, capsules, pills, powders, aqueous or oily solutions or suspensions, emulsions, and sterile injectable aqueous or oily solutions or suspensions.

In general compositions for oral administration are preferred.

The compositions may be obtained using standard excipients and procedures well known in the art. A unit dose form such as a tablet or capsule will usually contain, for example 0.1–2.50 mg of active ingredient. The compositions may also contain other active ingredients known for use in the treatment of obesity and related conditions, for example appetite suppressants, vitamins and hypoglycaemic agents.

In a preferred aspect of the present invention, compounds of the formulae (I) and (II) may be formulated for oral administration in a sustained (or delayed) release composition, for example a matrix tablet formulation comprising insoluble or swellable polymeric filler, or a coated spheroid formulation. In this manner compounds of the formulae (I) and (II) are delivered, unchanged, to the gut whereupon they are released and subsequently pass into the bloodstream. A sustained release composition prolongs the duration of action of the compounds of this invention.

When used to produce thermogenic effects in warm-blooded animals including man, a compound of formulae (I)(or (II)), or a pharmaceutically acceptable salt thereof as appropriate, will be administered so that a does in the general range 0.002–20 mg/kg, and preferably in the range 0.02–10 mg/kg, is administered daily, given in a single dose or divided doses as necessary. However, it will be appreciated by those skilled in the art that dosage will necessarily be varied or appropriate, depending on the severity of the condition under treatment and on the age and sex of the patient and according to known medical principles.

In a further aspect the present invention provides a process for preparing a compound of the formula (I) or a pharmaceutically acceptable salt thereof which process comprises:

(a) reacting a compound of the formula (III) with a compound of the formula (IV):

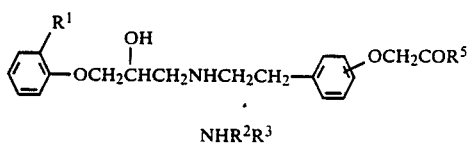  (III)

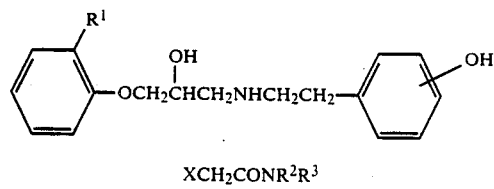  (IV)

wherein R¹-R³ are as hereinbefore defined and R⁵ is a displaceable group; or (b) reacting a compound of the formula (V) with a compound of the formula (VI):

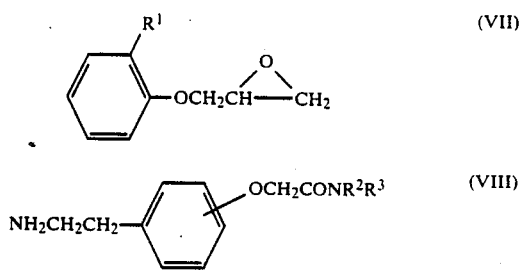  (V)

(VI)

wherein R¹—R³ are as hereinbefore defined and X is a leaving group; or (c) reacting a compound of the formula (VII) with a compound of the formula (VIII):

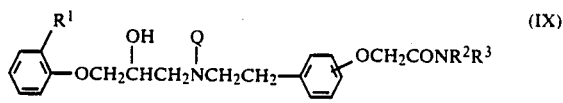  (VII)

(VIII)

wherein R¹-R³ are as hereinbefore defined; or (d) deprotecting a compound of the formula (IX)

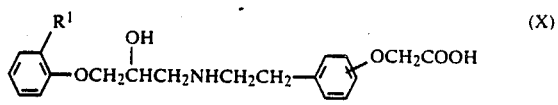  (IX)

wherein R¹ -R³ are as hereinbefore defined and Q is a protecting group: or (e) reacting a suitably protected compound of the formula (X) or activated derivative thereof:

(X)

wherein R¹ is as hereinbefore defined with a compound of the formula (IV) as hereinbefore defined; and thereafter, if necessary, forming a pharmaceutically acceptable salt.

The reaction of the compounds of the formulae (III) and (IV) is generally performed in a suitable substantially inert solvent for example a $C_{1-4}$ alkanol such as methanol or ethanol, at a non-extreme temperature for example in the range 0°-80 C. The reaction is optionally performed in a pressure vessel when a volatile amine is used. The compound of the formula (IV) is conveniently present as an excess.

Particularly suitable values of R⁵ include $C_{1-6}$ alkoxy for example methoxy and ethoxy, phenoxy and benzyloxy. Preferably R⁵ is methoxy or ethoxy.

The compounds of the formula (III) may be prepared by deprotecting a compound of the formula (XI):

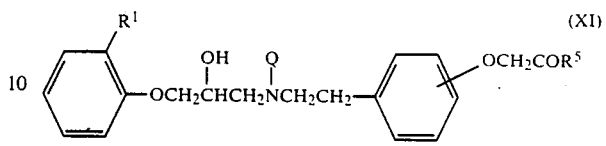  (XI)

wherein Q is a protecting group and R¹ and R⁵ are as hereinbefore defined. Protecting groups Q and methods of deprotection are analogous to those described hereinbelow for the deprotection of compounds of the formula (IX) The compounds of the formula (XI) may be prepared in any convenient manner, for example by reacting a compound of the formula (XIII) as defined hereinafter, with a compound of the formula: $XCH_2COR^5$ wherein X and R⁵ are as hereinbefore defined and subsequently reacting the product with a compound of the formula (VII). Such reactions are performed by methods similar to those described herein for analogous reactions.

In an alternative the compounds of the formula (III) may be prepared by reacting a compound of the formula (V) with a compound of the formula $XCH_2COR^5$ wherein X is a leaving group and R⁵ is as hereinbefore defined. Such reaction is performed analogously to the reaction between compounds of the formulae (V) and (VI) as described hereinbelow.

In the compounds of the formula (VI) X is a leaving group, for example chloro, iodo, bromo, methanesulphonyloxy or p-toluenesulphonyloxy. The reaction of the compounds of the formulae (V) and (VI) is conveniently performed in the presence of an external base, for example an inorganic base such as an alkali metal carbonate or acetate (for example potassium carbonate or sodium acetate), or an alkali metal hydride (e.g sodium hydride), and at a temperature in the range, for example, 10° to 120° C. A suitable solvent or diluent, for example acetone, methyl ethyl ketone, propan-2-ol, 1,2-dimethoxyethane or t-butyl methyl ether may conveniently be used. In order to minimise side-reactions, the process may also be carried out by pre-reacting the phenol of the formula (V) with a suitable base for example potassium tert-butoxide, to form the corresponding salt which is then added to the alkylating agent of the formula $XCH_2CONR^2R^3$.

The compounds of the formula (V) may be obtained by conventional procedures of organic chemistry, see for example EP-A-140243 and methods analogous thereto. Thus, for example, they may be obtained by reaction of a phenol of the formula (XII):

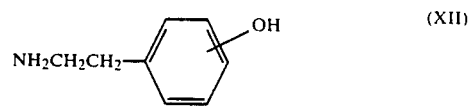  (XII)

with an epoxide of the formula (VII) in a suitable solvent, for example, an alcohol such as ethanol or propan-2-ol, at a temperature in the range, for example, 10° to 110° C. and conveniently at or near the boiling point of the reaction mixture. The epoxides of the formula (VII)

are known per se but can be made by reaction of phenol, o-chlorophenol or o-fluorophenol with epichlorohydrin or epibromohydrin in the presence of a suitable base such as an alkali metal hydroxide, piperidine, morpholine or N methylmorpholine, in a suitable solvent or diluent such as methanol, ethanol or propan-2 ol, conveniently at or near the boiling point of the reaction mixture.

In general, it is preferred to react the epoxide of the formula (VII) with a protected phenol derivative of the formula (XIII):

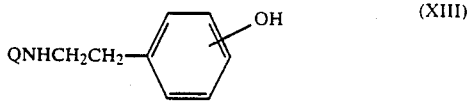
(XIII)

wherein Q is a suitable protecting group, such as benzyl. In this case, following the reaction of the compounds of the formulae (VII) and (XIII), the protecting group is removed, for example in the case of benzyl by hydrogenolysis, for example using hydrogenation at a pressure in the range, for example, 1 to 30 bar in the presence of a palladium-on-carbon catalyst in an inert diluent or solvent for example, a $C_{1-4}$ alkanol (such as methanol, ethanol or t-butyl alcohol) or a $C_{1-4}$ alkanoic acid (such as acetic acid) and at a temperature of for example 20°–80° C.

The reaction of the compounds of the formulae (VII) and (VIII) is conveniently performed under conditions generally similar to those described hereinabove for the reaction between the compounds of the formulae (VII) and (XII). The compounds of the formula (VIII) may be prepared by reacting a compound of the formula (XII) with a compound of formula (VI) under conditions generally similar to those described hereinabove for reacting compounds of the formulae (V) and (VI).

The deprotection of a compound of the formula (IX) may be performed in conventional manner for example by hydrogenolysis. Suitable hydrogenolysable groups Q include benzyl, 4-methoxybenzyl and 3,4-dimethoxybenzyl. Conveniently hydrogenation is performed at a pressure in the range 1–30 bar in the presence of a palladium catalyst, such as palladium on carbon, in a substantially inert solvent for example a $C_{1-4}$ alkanol (such as methanol, ethanol, isopropanol or t-butanol) or a $C_{1-4}$ alkanoic acid (such as acetic acid) and at a non-extreme temperature for example in the range 10°–80° C., conveniently room temperature.

The compounds of the formula (IX) may be prepared in a manner analogous to that described for the preparation of the compounds of the formula (I). For example a compound of the formula (VI) may be reacted with a compound of the formula (XIV):

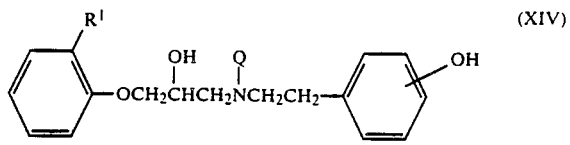
(XIV)

wherein Q is a protecting group for example benzyl, 4-methoxybenzyl or 3,4-dimethoxybenzyl and $R^1$ is as hereinbefore defined, in a manner analogous to that described hereinabove for reacting compounds of the formulae (V) and (VI). In an alternative a compound of the formula (XI) may be reacted with a compound of the formula (IV) under conditions similar to those described hereinabove for reacting compounds of the formulae (III) and (IV). In a further alternative the compounds of the formula (IX) may be prepared by reacting a compound of the formula (XV):

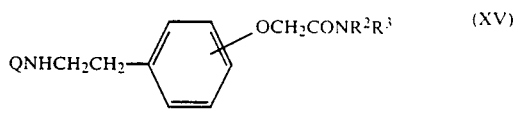
(XV)

wherein Q, $R^2$ and $R^3$ are as hereinabove defined, with a compound of the formula (VII) under conditions similar to those described hereinabove for reacting compounds of the formulae (VII) and (VIII).

The compounds of the formula (XIV) and (XV) are conveniently prepared by reacting a compound of the formula (XIII) with a compound of the formula (VII) or (VI) respectively under conventional reaction conditions. An example of a compound of the formula (XIII) is N-benzyltyramine readily prepared by reductive amination of benzaldehyde with tyramine.

In addition, compounds of the formula (IX) wherein $R^3$ is a group $OR^4$ wherein $R^4$ is other than hydrogen may be prepared by reacting a compound of the formula (IX) wherein $R^3$ is a group —OH with an alkylating agent (or arylating agent) under conventional alkylating conditions. For example, in general, O-alkylation is performed in the presence of an alkylating agent and about one equivalent of a suitable base. If $R^2$ is hydrogen, O,N-dialkylation is performed in the presence of an alkylating agent and about two equivalents of a suitable base. In particular a compound of the formula (IX) wherein $R^2$ and $R^4$ together form a $C_{3-4}$ methylene chain may be prepared by the alkylation of a compound of the formula (IX) wherein —$NR^2R^3$ is —NHOH with a compound of the formula: $L^1(CH_2)_nL^2$ wherein n is 3 or 4 and $L^1$ and $L^2$ are both leaving groups. Reference may also be made to EP-A-140243 and EP-A-210849 which detail the preparation of certain N benzyl compounds.

The reaction between the suitably protected compound of the formula (X) or activated derivative thereof and the compound of the formula (IV) is performed under conventional conditions, for example under standard acylation conditions wherein the acid is activated as the acid bromide, the acid chloride, an anhydride or activated ester, or the reaction is performed in the presence of a coupling agent such as dicyclohexylcarbodi-imide. The acid of the formula (X) is suitably protected prior to reaction, for example by benzylation on the nitrogen atom (reductive alkylation with benzaldehyde) and silylation on the hydroxy group. Protecting groups can, of course, be removed in conventional manner upon completion of the acylation or coupling reaction.

The compounds of the formula (X) are useful novel intermediates, and, of course, correspond to the compounds of the formula (II) which possess thermogenic activity. The use of such compounds as intermediates represents yet a further aspect of the present invention.

The compounds of the formula (X) (and (II)) may be prepared by methods analogous to those described for the preparation of compounds of the formula (I), using standard protecting groups as appropriate. In particular, it is preferred to convert a compound of the formula (III) wherein $R^5$ is a displaceable group such as $C_{1-6}$ alkoxy, phenoxy or benzyloxy to the free acid of the formula (X) (or (II)). In a preferred method, the compound of the formula (III) is hydrolysed under enzymic, acid or base conditions. Suitable acid conditions are for example a strong mineral acid such as hydrochloric, sulphuric or phosphoric acid, conveniently at a temperature in the range, for example, 20° to 110° C. and in a polar solvent, such as water, a $C_{1-4}$alkanol (for example methanol or ethanol) or acetic acid. In such cases, the corresponding mineral acid salt of the compound of formula (II) may be conveniently isolated. Alternatively, base conditions may be used, for example lithium, sodium or potassium hydroxide, conveniently in a suitable solvent or diluent such as an aqueous $C_{1-4}$alkanol at a temperature in the range, for example, 10° to 110° C. As yet further alternatives, when $R^5$ is t-butoxy, the decomposition may be carried out, for example, by thermolysis at a temperature in the range, for example, 100° to 220° C., alone or in the presence of a suitable diluent such as diphenyl ether; or, when $R^5$ is benzyloxy, by hydrogenolysis.

Pharmaceutically acceptable salts may be prepared by reacting the compound of the formula (I) or (II) with the appropriate acid in conventional manner. Alternatively when a hydrogen halide salt is required, it may conveniently be obtained by hydrogenation of the free base together with a stoichiometric amount of the corresponding benzyl halide.

The following biological test methods, data and Examples serve to illustrate this invention.

The thermogenic effects of the compounds of the formulae (I) and (II) may be demonstrated using one or more of the following standard tests:

(a) Rats are cold adapted by being placed in a cold environment (4° C.) for 10 days in order to increase their capacity for thermogenesis. They are then transferred to a thermoneutral environment (29° C.). Three hours later the core temperature is measured to determine a base-line reading and the test compound is administered sub-cutaneously or orally as a solution or suspension in 0.45% w/v aqueous sodium chloride, 0.25% w/v Polysorbate 80. After one hour, the core temperature is again measured. In this test, a compound which causes a statistically significant increase in the core-temperature of about 0.3° C. (or more) at a sub-cutaneous dose of 15 mg/kg (or less) is considered to be significantly active. The test acts as a model for the depressed thermogenesis which occurs during dieting.

(b) Rats are cold adapted at 4° C. for 4 days to increase their capacity for thermogenesis. They are then transferred to a warm environment of 23° C. for 2 days. On the following day, a test compound is administered sub-cutaneously or orally as described in (a). Animals are sacrificed one hour later and the interscapular, brown adipose tissue (BAT) pad is removed. BAT mitochondria are prepared by differential centrifugation and GDP binding is determined (Holloway et al., *International Journal of Obesity*, 1984, 8, 295) as a measure of thermogenic activation. Each test includes a control which is dosed with the solution/suspension vehicle only and a positive control which is dosed with isoprenaline (as its sulphate) at 1 mg/kg. Test compounds are routinely dosed at 0.1, 0.3, 1.0, 3.0, and 10 mg/kg and results expressed in terms of the effect on GDP binding produced by isoprenaline. From these results, a dose ($ED_{50}$) necessary to produce 50% of the isoprenaline effect is calculated by linear regression analysis. Compounds are considered active in this test if they cause a significant elevation in GDP binding as compared to controls. This test serves to indicate that the thermogenic effects observed in test (a) are mediated through an increase in effect on BAT rather than by some non-specific or toxic mechanism.

(c) Rats are adapted to a thermoneutral environment (29° C.) for 2 weeks in order to decrease their capacity for BAT mediated non-shivering thermogenesis. During the final 3 days the animals are trained to use an apparatus for measuring heart rate non-invasively via foot-pad electrodes connected to an ECG integrator giving a continuous read-out of heart rate. A test compound is administered sub-cutaneously or orally at the $ED_{50}$ determined in test (b), and heart rate is determined 15–30 minutes after dosing. The procedure is then repeated in subsequent tests using increasing multiples of the $ED_{50}$ determined in test (b) until the heart rate (HR) reaches or exceeds 500 beats per minute, allowing the dose necessary to produce a heart rate of 500 beats per minute ($D_{500}$ dose) to be calculated.

The ratio of $D_{500}$ to $ED_{50}$ in test (b) can be defined as the selectivity index (SI) and provides a measure of the selectivity of the compound for BAT as opposed to the cardiovascular system. Compounds are considered to have significant selectivity which have an SI of $>1$. Non-selective compounds have an SI of $<1$ (for example isoprenaline=0.06).

(d) Rats are cold adapted at 4° C. for four days to increase their capacity for thermogenesis. They are then transferred to a warm environment at 23° C. for two days. On the following day, the basal metabolic rate of the animals is determined using a close-circuit oxygen consumption apparatus of the type described by Arundel et al., 1984, *J. Appl. Physiol. Resoirat. Environ. Exercise Physiol.*, 1984, 57 (5) 1591–1593. The rats are then dosed (orally or sub-cutaneously) with test compound at about (10 mg/kg) as a solution or suspension in 0.45% w/v aqueous sodium chloride, 0.25% w/v Polysorbate 80. Metabolic rate is then determined for at least one hour after dosing. Compounds are considered active in this test if they cause a significant increase in metabolic rate as compared to control animals (Student's t test: p $<0.5$) dosed only the solution or suspension vehicle.

In the above tests, the compounds of the formula (I) in general produce effects of the following order without producing overt toxicity:

test (a): increase in core temperature of about 0.5° C. (or more) following a sub-cutaneous dosage of $<15$ mg/kg;

test (b): sub-cutaneous or oral $ED_{50}$ for GDP binding in BAT mitochondria of 0.01–10 mg/kg; and test (c): show an SI of $>50$.

By way of illustration, the compound described in the accompanying Example 24, produced the following effects in the above tests:

(a) +1.35° C. at a sub-cutaneous dose of 10 mg/kg;

(b) oral $ED_{50}$ 0.39 mg/kg;

(c) $D_{500}$: $>38.6$ mg/kg (oral); SI $>100$ (oral).

The invention will now be illustrated by the following Examples in which, unless otherwise stated:

(a) nuclear magnetic resonance (NMR) spectra were determined at 200 MHz unless otherwise stated, in $d_6$-dimethylsulphoxide/$d_4$-acetic acid as solvent using tetramethylsilane (TMS) as an internal standard and are expressed in delta values (parts per million) for protons relative to TMS, using conventional abbreviations to describe signal types.

(b) all crystalline end-products had satisfactory microanalyses.

(c) chromatography was performed on Merck Kieselgel (art 7734) obtainable from E Merck, Darmstadt, Federal Republic of Germany.

(d) where noted, solutions were taken to low pH as judged by moist indicator paper.

EXAMPLE 1

Methyl 4-[2-(2-hydroxy-3-phenoxypropylamino)ethyl]-phenoxyacetate hydrochloride (3.0 g) was suspended in 2N hydrochloric acid (150 ml) and heated on the steam bath for 2 hours. A clear solution was produced, from which the product crystallised on cooling. The crystals were filtered off, washed with a small volume of 2N hydrochloric acid followed by ether, and dried over phosphorus pentoxide. Thus was obtained 4-[2-(2-hydroxy-3-phenoxypropylamino)-ethyl]phenoxyacetic acid hydrochloride (2.04 g) mp 192°–94° C.; NMR 2.86–3.33[m,6H, $CH_2NHCH_2CH_2$]: 4.02[m,2H, $PhOCH_2$]; 4.22[m,1H,$CHOH$]; 4.63[s,2H, $OCH_2CO$]; 6.84–7.38[m,9H, aromatic H]: microanalysis: found C, 59.8; H, 6.3; N, 3.5; Cl, 9.3%; $C_{19}H_{23}NO_5$·HCl requires: C, 59.8; H, 6.3; N,3.7; Cl, 9.3%.

The starting material was prepared by dissolving methyl 4-[2-(N-benzyl-N-(2-hydroxy-3-phenoxypropyl)amino)ethyl]phenoxyacetate (3.0 g) (see Example 8) in methanol (150 ml), adding ethereal hydrogen chloride dropwise to give a pH of 3, followed by 10% palladium on carbon (250 mg). The mixture was stirred under an atmosphere of hydrogen for 16 hours. The catalyst was removed by filtration through diatomaceous earth and the filtrate evaporated to give methyl 4-[2-(2-hydroxy-3-phenoxypropylamino)ethyl]phenoxyacetate hydrochloride (3.0 g) in the form of a gum, which was used directly and without further purification

EXAMPLE 2

Following a procedure analogous to that of Example 1 (wherein the starting material is prepared according to Example 8) but using (S) phenylglycidyl ether as starting material, there was obtained 4-[2-(2S-hydroxy-3-phenoxypropylamino)ethyl]phenoxyacetic acid hydrochloride, mp 196°–7°; $\alpha_D$-18.2°(c=1, $CH_3OH$): microanalysis: found: C,59.3; H,6.2; N,3.6%; $C_{19}H_{23}NO_5$HCl·0.25% $H_2O$ requires: C,59.1; H,6.3; N,3.6%: NMR: 400 MHz 2.87–3.00[m,2H,$CH_2C_6H_4$]; 3.02,3.06[pr.d,1H, one of $CHOHCH_2NH$]; 3.10–3.2[m,2H,$NHCH_2CH_2$]; 3.18–3.21[pr.d,1H, one of $CHOHCH_2NH$]; 3.97[septet, 2H, $OCH_2CHOH$]; 4.21[m,1H,$CHOH$]; 4.63[s,2H,$OCH_2CO$]; 6.82–7.0[m,5H, aromatic H]; 7.12–7.35[m,4H, aromatic H].

EXAMPLE 3

A mixture of 4-[2-(Nbenzyl-N-(2-hydroxy-3-phenoxypropyl)amino)ethyl]phenoxyacetic acid (3.0 g), hydroxybenztriazole (2.25g), dicyclohexylcarbodiimide (1.9 g) and 3-methoxypropylamine (1.0 g) in dimethylformamide (25 ml) was stirred at room temperature for 16 hours. Ether (50 ml) was added and dicyclohexylurea filtered off. The filtrate was evaporated under reduced pressure. Toluene was added to the residue and volatile material was evaporated. This process was repeated twice to give a thick oil (4.8 g) which was purified by chromatography on K60 silica (260 g) using 2% methanol in dichloromethane as eluant. Thus was obtained N-3-methoxypropyl 4-[2-(Nbenzyl-N-(2-hydroxy-3-phenoxypropyl)amino)ethyl]phenoxyacetamide (2.8 g) which was contaminated with dicyclohexylurea. NMR 1.66[quintet, 2H,$CH_2CH_2CH_2$]; 2.60–2.86[m,6H, $CHOHCH_2NCH_2CH_2$]; 3.14–3.26[m,5H,$CONHCH_2$ and $CH_3$]; 3.30[t,2H,$CH_2OCH_3$]; 3.72–4.06[m,5H,$OCH_2CHOH$ and $CH_2Ph$]; 4.37[s,2H,$OCH_2CO$]; 6.77–7.40[m,14H, aromatic H].

N-3- Methoxypropyl 4-[2-(N-benzyl-N-(2-hydroxy-3-phenoxypropyl)amino)ethyl]phenoxyacetamide (2.7g) was dissolved in methanol (130 ml) and acidified to pH3 with an ethereal solution of hydrogen chloride. 10% Palladium on carbon (440 mg) was added and the mixture stirred under an atmosphere of hydrogen for 4 hours. The mixture was filtered through diatomaceous earth and the filtrate evaporated to give a crude product, which was purified by chromatography on K60 silica (55 g) using 10% methanol in dichloromethane as eluant. The product was dissolved in dichloromethane and ethereal hydrogen chloride added to give a pH of 3. The solvent was evaporated and the residue dissolved in dichloromethane which was also evaporated. The residue (1.4 g) was recrystallised from methyl acetate (50 ml) and methanol (15 ml). Thus was obtained N-3-methoxypropyl 4-[2-(2-hydroxy-3-phenoxypropylamino)ethyl]phenoxyacetamide (0.75 g), m.p. 167°9°, the NMR data were consistent with those of Example 11.

The starting material was prepared as follows: Methyl 4-[2-(N-benzyl-N-(2-hydroxy-3-phenoxypropyl)amino)ethyl]phenoxyacetate (3.1 g) was dissolved in methanol (100 ml) and treated with a solution of sodium hydroxide (0.5 g) in water (3 ml). The mixture was heated to reflux for 30 minutes. The solvent was evaporated and the residue was dissolved in water (50 ml) and extracted with ether (50ml). The aqueous solution was acidified to pH2 with 2N hydrochloric acid and the product extracted with ethyl acetate (4×100 ml). The extracts were evaporated, and the residue was azeotroped with toluene, to give 4-[2-(Nbenzyl-N-(2-hydroxy-3-phenoxypropyl)amino)ethyl]phenoxyacetic acid (3.0 g) NMR: 2.83–3.20(m,6H, $CHOHCH_2NCH_2CH_2$]; 3.90[m,2H,$OCH_2CHOH$]; 4.12–4.28[m,3H,$CHOH$ and $CH_2C_6H_5$]; 4.60[s,2H,$OCH_2CO$]; 6.76–7.56[m,14H, aromatic H]. The product was contaminated with a trace of toluene.

EXAMPLE 4

To a solution of N3-methoxypropyl 4-[2-(Nbenzyl-N-(2S-hydroxy-3-phenoxypropyl)amino)ethyl]phenoxyacetamide (6.0 g) in methanol (100 ml) was added catalyst (10% Pd/C (0.5 g)) and the mixture was hydrogenated in an atmosphere of hydrogen overnight. The mixture was filtered through diatomaceous earth under an inert atmosphere (argon) and the filtrate evaporated to dryness under reduced pressure, giving a colourless solid (4.5 g). This was dissolved in methanol and the solution acidified to <pH3 by adding a saturated solution of HCl in ether. The mixture was evaporated under reduced pressure to dryness and redissolved in methanol and again evaporated under reduced pressure. This cycle was repeated once more, to give N-(3-methoxypropyl 4-[2-(2S-hydroxy-3-phenoxypropylamino)ethyl] phenoxyacetamide hydrochloride (4.4 g) as colourless platelets, m.p. 168°–169° C., $[\alpha]_D$ −15.3° (c=1, MeOH) NMR; identical with that of Example 11.

The starting material was made as follows: A solution of (S)-phenylglycidyl ether (2.45 g) and N-3-methoxypropyl 4-[2-(Nbenzylamino)ethyl]phenoxyacetamide (5.28 g) in isopropanol (30 ml) was stirred at room temperature for 4 days. The mixture was evaporated under reduced pressure and the residue dissolved in toluene, then evaporated again. This cycle was repeated three times to give an almost colourless oil (8.7 g) which was chromatographed on silica gel using a gradient elution of 1–5% methanol in dichloromethane to give N3-methoxypropyl 4-[2-(N-benzyl-N-(2S-hydroxy-3-phenoxypropyl)amino)ethyl]phenoxyacetamide (6.5 g) as a colourless oil.

N3-Methoxypropyl 4-[2-(Nbenzylamino)ethyl]-phenoxyacetamide was prepared by reacting methyl 4-[2-(N-benxylamino)ethyl]phenoxyacetate hydrochloride (10 g) with excess 3-methoxypropylamine (15 ml) in methanol (75 ml). The initial suspension dissolved on stirring at room temperature and the reaction mixture was stirred overnight. The solvent was evaporated under reduced pressure to give a colourless oil which was partitioned between ethyl acetate and water. The organic phase was separated, washed with water (3×) then with brine (1×), then dried over MgSO4. Evaporation under reduced pressure gave N3-methoxypropyl 4-[2-(Nbenzylamino)ethyl]-phenoxyacetamide (10.5 g) as a colourless oil.

EXAMPLE 5

Following the same procedure as described in Example 4, N3-ethoxypropyl 4-[2-(Nbenzyl-N-(2-hydroxy-3-phenoxypropyl)amino)ethyl]-phenoxyacetamide (1.8 g) was hydrogenated in propan-2-ol (100 ml) to provide a colourless solid (1.5 g) which was recrystallised from propan-2-ol to give N 3-ethoxypropyl 4-[2-(2-hydroxy-3-phenoxypropylamino)ethyl]phenoxyacetamide hydrochloride (1.05 g) as a colourless solid, mp 166°–168° C.; NMR 1.13[t,3H,CH$_3$]; 1.72 [quintet, 2H, CH$_2$CH$_2$CH$_2$); 2.95–3.10[m,2H, CH$_2$C$_6$H$_4$]; 3.10–3.5[m,10H, CH$_2$NHCH$_2$ plus NHCH$_2$CH$_2$CH$_2$OCH$_2$]; 3.95–4.12[m,2H, OCH$_2$CHOH]; 4.23–4.38(m,H,CHOH); 4.50[s,2H, OCH$_2$CO); 6.85–7.05[m,5H, aromatic H]; 7.15–7.40[m,4H, aromatic H].

The starting material, N-3-ethoxypropyl 4-[2-(N-benzyl-N-(2-hydroxy-3-phenoxypropyl)amino)ethyl]-phenoxyacetamide was prepared, in a manner similar to that of Example 4, by the reaction of 3-ethoxypropylamine (1.0 g) with methyl 4-[2-(Nbenzylamino)ethyl]-phenoxyacetate hydrochloride (1.7 g) in methanol (50 ml) to give N-3-ethoxypropyl 4-[2-(N-benzylamino)ethyl]phenoxyacetamide as a colourless oil. This was reacted with phenylglycidyl ether, in a manner similar to Example 4, to give the desired compound

EXAMPLE 6

In a manner analogous to Example 5, 2-methoxyethylamine was reacted with methyl 4-[2-(Nbenzylamino)ethyl]phenoxyacetate hydrochloride to give N2-methoxyethyl 4-[2-(Nbenzylamino)ethyl]-phenoxyacetamide. This was reacted with phenylglycidyl ether to afford N-2-methoxyethyl 4-[2-(N-benzyl-N-(2-hydroxy-3-phenoxypropyl)amino/ethyl]phenoxyacetamide which was hydrogenated (as in Example 5) to give N-2-methoxyethyl 4-[2-(2-hydroxy-3-phenoxypropylamino)ethyl]phenoxyacetamide which crystallised from methanol as a colourless solid, mp 168°–170° C.; NMR: 2.92–3.06[m, 2H, CH$_2$C$_6$H$_4$]; 3.06–3.45[m, 8H, CH$_2$NHCH$_2$ plus CH$_2$CH$_2$O]; 3.26[s,3H, OCH$_3$]; 4.02[m,2H, OCH$_2$CHOH]; 4.28[m,1H, CHOH]; 4.48[s, 2H, OCH$_2$CO]; 6.90–7.02[m,5H, aromatic H]; 7.16–7.36[m,4H, aromatic H].

EXAMPLE 7

In a manner analogous to Example 5, N-ethyl-N-methylamine was reacted with methyl 4-[2-(Nbenzylamino)ethyl]phenoxyacetate hydrochloride to give N-ethyl-N-methyl 4-[2-(N-benzylamino)ethyl]-phenoxyacetamide. This was reacted with phenylglycidyl ether to afford N-ethyl-N-methyl 4-[2-(N-benzyl-N-(2-hydroxy-3-phenoxypropyl)amino)ethyl]phenoxyacetamide which was hydrogenated (as in Example 5) to give methyl 4-[2-(2-hydroxy-3-phenoxypropylamino)-ethyl]-phenoxyacetamide which crystallised from propan-2-ol to give a colourless solid, mp 117°–9° C.; NMR: 1.07–1.18[pr.t, hindered rotamers, 3H, CH$_2$CH$_3$]; 2.88–3.00[pr.s, hindered rotamers, 3H, NCH$_3$]; 2.95–3.10[m, 2H, CH$_2$C$_6$H$_4$]; 3.10–3.46[m, 6H, CH$_2$NHCH$_2$ plus NCH$_2$CH$_3$]; 4.03[m, 2H, OCH$_2$CHOH]; 4.34[m, 1H, CHOH]; 4.75–4.77[d, hindered rotamers, 2H, OCH$_2$CO]; 6.85–7.03[m, 5H, aromatic H]; 7.15–7.36[m, 4H, aromatic H].

EXAMPLE 8

A solution of methyl 4-[2-(N-benzyl-N-(2-hydroxy-3-phenoxypropyl)amino)ethyl]phenoxyacetate (6.0 g) and piperidine (16 ml) in methanol (60 ml) was stored at room temperature for 4 days. The solvent and excess reagent were evaporated under reduced pressure. Toluene was added to the residue and volatile material was evaporated. This procedure was repeated twice more. The crude intermediate (8.0 g) was purified by chromatography on K60 silica (210 g) using a mixture of methanol and dichloromethane of increasing polarity (1% to 2% methanol) to give N-(4-[2-(N-benzyl-N-(2-hydroxy-3-phenoxypropyl)amino)ethyl]phenoxyacetyl)piperidine (6.2 g) as a gum. The purified intermediate (6.2 g) was debenzylated in an analogous manner to that of Example 23, to give a colourless solid (5.1 g) which was recrystallised from propan 2-ol to yield N-(4-[2-(2-hydroxy-3-phenoxypropylamino)ethyl]phenoxyacetyl)-piperidine hydrochloride (3.7 g) m.p. 139°–41°; NMR: 1.40–1.70[m,6H, CH$_2$(CH$_2$)$_3$CH$_2$]; 2.90–3.10[m,2H, CH$_2$C$_6$H$_4$]; 3.10–3.35[m,4H, CH$_2$NHCH$_2$]; 3.35–3.55[m,4H, CH$_2$NCH$_2$]; 4.03[m,2H,PhOCH$_2$]; 4.30[m,1H,CHOH]; 4.75[s,2H, OCH$_2$CO]; 6.85–7.05[m,5H, aromatic H]; 7.15–7.38[m,4H, aromatic H]: microanalysis: found: C, 64.2; H, 7.4; N, 5.8; Cl, 7.7%; C$_{24}$H$_{32}$N$_2$O$_4$.HCl requires: C, 64.2; H, 7.4; N, 6.2; Cl 7.9%.

The starting material was obtained as follows: N-Benzyltyramine (9.08 g) was added to a stirred solution of potassium t-butoxide (4.5 g) in dimethoxyethane (80 ml). To the clear solution was added methyl bromoacetate (6.2 g) and the mixture was stirred overnight. The mixture was diluted with ether (250 ml) and washed with water (2×25 ml). The ethereal solution was dried (MgSO$_4$) and evaporated, to give methyl 4-[2-(benzylamino)ethyl]phenoxyacetate (15.0 g) as an oil, which was dissolved in isopropanol and teated with phenylglycidyl ether (7.5 g). The solution was heated to reflux for 1 hour, and then evaporated. The residue was dissolved in toluene and volatile material evaporated before being purified by chromatography on K60 silica (220 g) using 1% methanol in dichloromethane. Methyl 4-[2-(N-benzyl-N-(2-hydroxy-3-phenoxypropyl)amino)ethyl]phenoxyacetate was obtained as an oil (9.5 g), NMR: 2.55–2.85[m,6H, CH$_2$NHCH$_2$CH$_2$];

3.65–4.05[m,8H, PhOCH$_2$CHOH and PhCH$_2$ and OCH$_3$]; 4.67]s, 2H, OCH$_2$CO]; 6.73–7.40[m, 14H, aromatic H].

EXAMPLES 9–16

Using a procedure similar to that described in Example 8 but using the appropriate amine the following compounds were obtained, in each case isolated as a hydrochloride salt.

$$\text{Ph—OCH}_2\text{CHCH}_2\text{NHCH}_2\text{CH}_2\text{—C}_6\text{H}_4\text{—OCH}_2\text{CONR}^2\text{R}^3$$
(OH on central C)

| Example | R$^2$ | R$^3$ | m.p. (°C.) | recrystallisation solvent |
|---|---|---|---|---|
| 9 | —CH$_3$ | H | 208–210 | methanol/methyl acetate |
| 10 | —C$_2$H$_5$ | H | 202–4 | methanol/methyl acetate |
| 11 | —(CH$_2$)$_3$OCH$_3$ | H | 167–9 | methanol/methyl acetate |
| 12 | -cyclopropyl | H | 198–200 | methanol |
| 13 | —(CH$_2$)$_4$CH$_3$ | H | 196–8 | methanol/ether |
| 14 | —CH$_3$ | CH$_3$ | 130–2 | methanol/ether |
| 15 | —(CH$_2$)$_5$CH$_3$ | H | 195–7 | methanol/ether |
| 16 | —CH$_2$CONH$_2$ | H | 209–11 | methanol |

NMR Data

EXAMPLE 9

2.64[s,3H,CH$_3$]; 2.85–3.00[m,2H,CH$_2$C$_6$H$_4$]; 3.00–3.25[m,4H,CH$_2$NHCH$_2$]; 3.96[m,2H,OCH$_2$CHOH]; 4.19[m,1H,CHOH]; 4.40[s,2H,OCH$_2$CO]; 6.84–6.96[m,5H, aromatic H]; 7.0–7.33[m,4H, aromatic H].

EXAMPLE 10

1.05[t,3H,CH$_2$CH$_3$]; 2.88–3.05[m,2H,CH$_2$C$_6$H$_4$]; 3.05–3.30[m,6H,CH$_2$NHCH$_2$;$_2$NHCH$_2$ plus NHCH$_2$CH$_3$]; 4.00[m,2H,OCH$_2$CHOH]; 4.23[m,1H,CHOH]; 4.45[s,2H,OCH$_2$CO]; 6.88–7.02[m,5H, aromatic H]; 7.15–7.38[m, 4H, aromatic H].

EXAMPLE 11

1.65[q,2H, CH$_2$CH$_2$CH$_2$]; 2.82–3.00[m,2H,CH$_2$C$_6$H$_4$]; 3.00–3.34[m, 8H, CH$_2$NHCH$_2$ plus NHCH$_2$CH$_2$O]; 3.15[s,3H,OCH$_3$]; 3.95[m,2H,OCH$_2$CHOH]; 4.18[m,1H,CHOH]; 4.40[s,2H,OCH$_2$CO]; 6.84–6.96[m,5H, aromatic H]; 7.10–7.33[m,4H, aromatic H].

EXAMPLE 12

0.45–0.71[m,4H, CHCH$_2$CH$_2$]; 2.68[m,1H,NHCH]; 2.87–3.04[m,2H,CH$_2$C$_6$H$_4$]; 3.04–3.30[m,4H, CH$_2$NHCH$_2$]; 3.98[m,2H,OCHCHOH]; 4.22[m,1H,CHOH]; 4.42[s,2H,OCH$_2$CO]; 6.85–7.05[m,5H, aromatic H]; 7.15–7.38[m,4H, aromatic H].

EXAMPLE 13

0.86[5,3H,CH$_3$]; 1.15–1.35[m,4H,CH$_2$CH$_2$CH$_3$]; 1.35–1.55[quintet, 2H, NHCH$_2$CH$_2$CH$_2$]; 2.85–3.05[m,2H,CH$_2$C$_6$H$_4$]; 3.05–3.30[m,6H,CH$_2$NHCH$_2$ plus CONCH$_2$]; 4.00[m,2H, OCH$_2$CHOH]; 4.20[m,1H,CHOH]; 4.45[s,2H,OCH$_2$CO]; 6.88–7.02[m,5H, aromatic H]; 7.15–7.35[m,4H, aromatic H].

EXAMPLE 14

2.85[s,3H,N–CH$_3$]; 3.0[s,3H,N-CH$_3$]; 2.85–3.30[m,6H,CH$_2$NHCH$_2$CH$_2$]; 3.98[m,2H, OCH$_2$CHOH]; 4.22[m,1H,CHOH]; 4.75[s,2H,OCH$_2$CO]; 6.84–7.04[m,5H, aromatic H]; 7.10–7.38[m,4H, aromatic H].

EXAMPLE 15

0.86[t,3H,CH$_3$]; 1.25[s,6H, CH$_2$CH$_2$CH$_2$CH$_3$]; 1.45[quintet, 2H, CONHCH$_2$CH$_2$]; 2.86–3.03[m,2H, CH$_2$C$_6$H$_4$]; 3.03–3.30[m,6H, CH$_2$NHCH$_2$ plus CONHCH$_2$]; 3.89[m,2H, OCH$_2$CHOH]; 4.24[m,1H, CHOH]; 4.45[s,2H,OCH$_2$CO]; 6.86–7.03[m,5H, aromatic H]; 7.14–7.40[m,4H, aromatic H].

EXAMPLE 16

2.85–3.05[m,2H, CH$_2$C$_6$H$_4$]; 3.05–3.30[m,4H,CH$_2$NHCH$_2$]; 3.75[s,2H, NHCH$_2$CO]; 3.98[m,2H,OCH$_2$CHOH]; 4.22[m,1H,CHOH]; 4.53[s,2H,OCH$_2$CO]; 6.88–7.04[m,5H, aromatic H]; 7.15–7.38[m,4H, aromatic H].

EXAMPLE 17

A mixture of methyl 4-[2-(2-hydroxy-3-phenoxypropylamino)ethyl]phenoxyacetate (0.47 g) and n-hexylamine (5 ml) in methanol (5 ml) was kept at room temperature for 24 hours. Solvent and excess reagent were evaporated. Toluene was added to the residue and volatile material was evaporated. The residue was triturated with ether, which was discarded, and dissolved in dichloromethane. Ethereal hydrogen chloride was added to pH3, and the dichloromethane evaporated and replaced with fresh dichloromethane which also was evaporated. The residue was recrystallised from methanol/ether to give N-n-hexyl-4-[2-(2-hydroxy-3-phenoxypropylamino)ethyl]-phenoxyacetamide hydrochloride (0.138 g) m.p. 192°–95° C.; NMR: 0.88[t,3H, CH$_3$(CH$_2$)$_5$]; 1.25[s,6H, (CH$_2$)$_3$CH$_3$]; 1.45[m,2H, CH$_2$(CH$_2$)$_3$CH$_2$]; 2.90–3.40[m,8H, CONHCH$_2$plus CH$_2$NHCH$_2$CH$_2$]; 4.00[m,2H, PhOCH$_2$]; 4.25[m,1H,CHOH]; 4.45[s,2H, OCH$_2$CO]; 6.9–7.4[complex, 9H, aromatic H]; microanalysis: found: C, 64.3; H, 8.2; N, 5.9; Cl, 7.0%; C$_{25}$H$_{36}$N$_2$O$_4$.HCl requires: C,64.6; H,8.0; N, 6.0;Cl, 7.6%.

The starting material was obtained as follows: Methyl 4-[2-(N-benzyl-N-(2-hydroxy-3-phenoxypropyl)amino)ethyl]-phenoxyacetate (1.9 g) was dissolved in dichloromethane (50 ml) and methanol (20 ml) and acidified to pH3 with ethereal hydrogen chloride. The solvent was removed by evaporation under reduced pressure, and replaced with methanol (150 ml). 10% Palladium on carbon (240 mg) was added, and the mixture stirred under an atmosphere of hydrogen for 3 hours. The catalyst was removed by filtration, and the filtrate evaporated to give a white solid (1.5 g), which was recrystallised from methanol to give methyl 4-[2-(2-hydroxy-3- phenoxypropylamino)-ethyl]phenoxyacetate hydrochloride (0.95 g) m.p. 159°–61° C.; NMR: 2.85–3.25 [m,6H, CH$_2$NHCH$_2$CH$_2$]; 3.66[s,3H, CH$_3$]; 3.95[m,2H,PhOCH$_2$]; 4.22[m,1H, CHOH]; 4.72[s,2H, OCH$_2$CO]; 6.82–6.98[m,5 aromatic H]; 7.12–H, 7.32[m,4H, aromatic H]: microanalysis: found: C, 60. H, 6.6; N, 3.5; 4; Cl, 8.8%; C$_{20}$H$_{25}$NO$_5$.HCl: C, 60.7; H, 6.6; N, 3.5; Cl, 9.0%.

EXAMPLES 18-20

Using a procedure similar to that described in Example 17 but using the appropriate amine compound of the formula (IV) the following compounds were obtained, in each case as a hydrochloride salt.

| Example | R² | R³ | m.p. (°C.) | recrystallisation solvent |
|---|---|---|---|---|
| 18 | —CH(CH₃)₂ | H | 203-5 | methanol/methyl acetate/ether |
| 19 | —CH₂C≡CH | H | 170-2 | methanol |
| 20 | —CH₂CH₂OCH₂CH₂— | | 135-7 | methanol/methyl acetate/ether |

NMR DATA

EXAMPLE 18

1.10[d,6H,(CH₃)₂]; 2.85-3.03[m,2H,CH₂C₆H₄]; 3.03-3.30[m,4H,CH₂NHCH₂]; 3.87-4.08[m,3H, OCH₂CHOH plus NHCH]; 4.21[m,1H,CHOH]; 4.42[s,2H,OCH₂CO]; 6.88-7.03[m,5H, aromatic H],7.13-7.38[m,4Haromatic H].

EXAMPLE 19

2.84-3.30[m,7H,CH₂NHCH₂CH₂plus ≡CH]; 3.90-4.06[m,4H,OCH₂CHOH plus CH₂C≡CH]; 4.22[m,1H,CHOH]; 4.50[s,2H,OCH₂CO]; 6.88-7.02[m,5H, aromatic H]; 7.15-7.38[m,4H, aromatic H].

EXAMPLE 20

2.86-3.00[m,2H,CH₂C₆H₄]; 3.00-3.28[m,4H, CH₂NHCH₂]; 3.45[br.d,4H,CH₂NCH₂]; 3.55[br.s,4H,CH₂OCH₂]; 3.98[m,2H,OCH₂CHOH]; 4.25[m,1H,CHOH]; 4.79[s,2H,OCH₂CO]; 6.83[m,5H, aromatic H]; 7.12-7.40[m,4H, aromatic H].

EXAMPLE 21

A solution of 4-(2-[(2-hydroxy-3-phenoxypropyl)amino]-ethyl)phenol (2.55 g) (Rzeszotarski et al., J. Med. Chem. 22, 735 (1979)) in dimethoxyethane (100 ml) was treated with potassium t-butoxide (1.1 g) and the mixture stirred at room temperature for 15 minutes. N-allyl-N-methylchloroacetamide (1.35 g) was added and the reaction mixture stirred for 2hours. The mixture was evaporated to small volume under reduced pressure, diluted with ether (200 ml), then washed with water (3×15 ml) and the organic phase dried over MgSO₄. Evaporation of the ether under reduced pressure gave a brown oil (3.4 g) which was dissolved in dichloromethane and acidified to pH3- by adding a saturated solution of HCl in ether. The mixture was evaporated to small volume under reduced pressure and the residue dissolved in dichloromethane. The solution was again evaporated and the cycle repeated once more. The residual oil (3.6 g) was crystallised from propan-2-ol (30ml) at −5° C. over 3 days. The colourless solid was filtered off and triturated with a small volume of propan-2-ol followed by methyl acetate. The air-dried solid (1.6 g) was recrystallised from propan-2-ol to give N-allyl-N-methyl-4-[2-(2-hydroxy-3-phenoxypropylamino)ethyl]phenoxyacetamide hydrochloride (0.4 g) mp 100°-102° C.; NMR 400 MHz 2.85 and 2.95[pr.s,3H, hindered rotamers, NCH₃]; 2.88-3.05[m,2H,CH₂C₆H₄]; 3.05-3.28[m,4H,CH₂NHCH₂]; 3.90-4.05[m,4H,OCH₂CHOH plus NCH₂CH]; 4.25[m,1H,CHOH]; 4.76 and 4.83[pr.s,2H, hindered rotamers, OCH₂CO]; 5.10-5.25[m,2H,CH=CH₂]; 5.68-5.95[m,1H,CH₂CH=CH₂]; 6.73-7.08[m,5H, aromatic H]; 7.14-7.36[m,4H, aromatic H].

EXAMPLE 22

In an analogous manner to Example 21, using N-(4-pyridylmethyl)chloroacetamide, instead of N-allyl-N-methylchloroacetamide, and allowing the reaction to stir overnight at room temperature, N-(4-pyridylmethyl)-4-[2-(2-hydroxy-3-phenoxypropylamino)ethyl]-phenoxyacetamide hydrochloride was obtained. This was recrystallised from propan-2-ol to give a colourless solid, mp 128°-130° C.; NMR 2.94-3.09[m,2H, CH₂C₆H₄]; 3.09-3.35[m,4H,CH₂NHCH₂]; 4.03[m,2H,OCH₂CHOH]; 4.30[m,1H,CHOH]; 4.65 and 4.68[pr.s,4H, OCH₂CO and NCH₂C₅H₄N]; 6.90-7.06[m,5H, aromatic H]; 7.19-7.48[m,4H, aromatic H]; 7.88-8.88[4H, pyridyl H].

The starting material was obtained as follows: A solution of 4-pyridylmethylamine (1.08 g) and triethylamine (1.0 g) in dichloromethane (25 ml) was added slowly over 30 minutes to a chilled, stirred solution of chloroacetyl chloride (1.2 g) in dichloromethane (7.5 ml). The reaction mixture was maintained at 0-5° C. throughout the addition, stirred for a further 30 minutes and allowed to warm to room temperature. The reaction mixture was washed with water (2×10 ml) and dried over MgSO₄. Evaporation of the solvent under reduced pressure gave N-(4-pyridylmethyl)-chloroacetamide as a brown oil, which was used immediately.

EXAMPLE 23

4-[2-(N-Benzyl-N-(2-hydroxy-3-phenoxypropyl)amino)ethyl]phenol (5.1 g) was added to a stirred solution of potassium t-butoxide (1.57 g) in dimethoxyethane (100 ml). To the resulting solution was added N,N-diethylchloroacetamide (2.1 g) and the mixture was stirred for two hours. The mixture was diluted with ether (300 ml) and washed with brine (2×20 ml). The solution was dried (MgSO₄) and evaporated under reduced pressure to yield the crude intermediate (12.5 g). The crude intermediate was purified by chromatography on K60 silica (225 g) using a gradient mixture of methanol and dichloromethane (1% to 3% of methanol) to give N,N-diethyl-4-[2-(N-benzyl-N-(2-hydroxy-3-phenoxypropyl)amino)ethyl]-phenoxyacetamide (6.6 g) as a gum. The gum was dissolved in methanol (400 ml) and treated with 10% palladium on carbon (380 mg). The mixture was stirred under an atmosphere of hydrogen for 4 hours. The catalyst was removed by filtration through Kieselguhr, and the filtrate evaporated to give the product (5.0 g) as a colourless oil, which was dissolved in dichloromethane (300 ml) and acidified to pH3with ethereal hydrogen chloride. The solvent was removed by evaporation and replaced with fresh dichloromethane which also was evaporated. The residual gum was dissolved in methyl acetate from which it crystallised as N,N-diethyl-4-[2-(2-hydroxy-3-phenoxypropylamino)ethyl]phenoxyacetamide hydrochloride (4.49 g) m.p. 113°-5° C.; NMR: 1.05[t,3H, CH₃]; 1.15[t,3H, CH₃]; 2.90-3.08[m,2H, CH₂C₆H₄]; 3.08-3.45(m,8H, CH₂NCH₂ +CH₂NHCH₂]; 4.0[m,2H,PhOCH₂]; 4.25[m,CHOH]; 4.75[s,2H,OCH₂CO]; 6.85-7.05[m,5H, aromatic H]; 7.25-7.4[m,4H, aromatic H]: microanalysis: found: C, 62.9; H,7.6; N, 6.1; Cl 8.3%; $C_{23}H_{32}N_2O_4 \cdot HCl$ requires: C, 63.2; H,7.6; N, 6.4; Cl 8.1%.

The starting material was obtained as follows:

A mixture of phenylglycidyl ether (8.0 g), N-benzyltyramine hydrochloride (13.0 g) and triethylamine (7.5 ml) in isopropanol (200 ml) was heated to reflux for 3 hours. The solvent was evaporated and toluene was added to the residue. Volatile material was evaporated. The residue was purified by chromatography on K60 silica (300 g) using a gradient mixture of methanol in dichloromethane (1 to 2% methanol). Thus was obtained 4-[2-(N-benzyl-N-(2-hydroxy-3-phenoxypropyl)amino)ethyl]phenol (16.5 g) as an oil which slowly crystallised, m.p. 103°–5° C.: NMR: 2.55–2.85[m,6H, CHCH$_2$NHCH$_2$CH$_2$]; 3.65–4.05 [m,5H, PhOCH$_2$CHOH +PhCH$_2$]; 6.65–7.4[m,14H, aromatic H].

EXAMPLES 24–25

Using a procedure similar to that described in Example 23 but using the appropriate chloroacetamide intermediate, the following compounds were obtained, in each case isolated as a hydrochloride salt.

OH
|
⟨⟩—OCH$_2$CHCH$_2$NHCH$_2$CH$_2$—⟨⟩—OCH$_2$CONR$^2$R$^3$

| Example | R$^2$ | R$^3$ | m.p. (°C.) | recrystallisation solvent |
|---|---|---|---|---|
| 24 | —(CH$_2$)$_2$OCH$_3$ | —CH$_3$ | 92–94° | Methyl acetate |
| 25 | —CH$_2$CON(CH$_3$)$_2$ | H | 145–7° | Propan-2-ol |

NMR DATA

EXAMPLE 24

2.85–3.55[m,16H,CH$_2$NHCH$_2$CH$_2$ and doubled signals for CH$_3$NCH$_2$CH$_2$OCH$_3$ hindered rotamers]4.00[m,2H,OCH$_2$CHOH]; 4.26[m,1H,CHOH]; 4.76, 4.83[pr.s. 2H,OCH$_2$CO hindered rotamers]; 6.83–7.03[m,5H, aromatic H]; 7.14–7.37[m,4H, aromatic H];

EXAMPLE 25

2.88[s,3H,CH$_3$]; 2.98[s,3H,CH$_3$]; 2.90–3.26[m,6H,CH$_2$NHCH$_2$CH$_2$]; 4.02[m,2H,OCH$_2$CHOH]; 4.06[s,2H,NCH$_2$CO]; 4.28[m,1H,CHOH]; 4.56[s,2H,OCH$_2$CO]; 6.90–7.04[m,5H, aromatic H]; 7.18–7.38[m,4H, aromatic H].

The required chloroacetamide for Example 24 was prepared as follows:

Chloroacetyl chloride (1.35 g) in dichloromethane (50 ml) was stirred in an ice-bath. A solution of N-methyl-N-(2-methoxyethyl)amine (1.067 g) and triethylamine (1.8 ml) in dichloromethane was added over 20 minutes. The reaction mixture was stirred for a further 30 minutes, then washed with water (1×20 ml, 2×15 ml) and dried over MgSO$_4$. The solvent was evaporated under reduced pressure to give N-(2-methoxyethyl)-N-chloroacetamide as a brown oil (1.8 g).

The required chloroacetamide for Example 25 was prepared as follows:

A solution of chloroacetyl chloride (1.7 g) in dichloromethane was stirred in an ice-bath, while a solution of N,N-dimethylglycinamide (1.8 g) and triethylamine (2.2 ml) in dichloromethane (20 ml) was added over 20 minutes. The reaction mixture was stirred for 30 minutes and was then washed with water (2×10 ml), and dried over MgSO$_4$. The solution was evaporated under reduced pressure. Thus was obtained N,N-dimethyl chloroacetylglycinamide (2.0 g) as a brown oil, which was used directly, and without further purification.

EXAMPLE 26

4-[2-(-N-Benzyl-N-(2-hydroxy-3-phenoxypropyl)amino)ethyl]phenol (1.93 g) was added to a stirred dispersion of 60% sodium hydride in mineral oil (0.25 g) in dimethylformamide (60 ml). After a period of 30 minutes. N,N-di-n-propylchloroacetamide (0.9 g) was added and the mixture stirred for 20 hours. The mixture was diluted with water (100 ml) and the product extracted into ether (1×100 ml, 3×50 ml). The extracts were dried over MgSO$_4$ and evaporated to give a light brown oil (3.6 g) which was purified by K60 chromatography using a mixture of 1% methanol in dichloromethane to give N,N-di-n-propyl-4-[2-(N-benzy-N-(2-hydroxy-3-phenoxypropyl)amino)ethyl]-phenoxyacetamide (1.9 g) as a gum.

The aforementioned gum was debenzylated in an analogous manner to that of Example 23. The crude product so obtained (1.3 g) was dissolved in dichloromethane and acidified to pH 3 with ethereal hydrogen chloride. The solvent was removed by evaporation under pressure and replaced with fresh dichloromethane which also was evaporated. The residue was dissolved in methyl acetate from which N,N-di-n-propyl 4-[2-(2-hydroxy-3-phenoxypropylamino)ethyl]-phenoxyacetamide hydrochloride crystallised as a colourless solid m.p. 104°–7° C.; NMR: 0.8–1.0[m,6H, 2×CH$_3$]; 1.4–1.7[m,4H, 2×CH$_2$CH$_3$]; 2.9–3.4 [m,10H, CH$_2$NHCH$_2$CH$_2$ plus CHHD 2NCH$_2$]; 3.95–4.1[m,2H, PhOCH$_2$]; 4.28[m,1H, CHOH]; 4.75[s,2H, OCH$_2$CO]; 6.8–7.4[m, 9H, aromatic H]; microanalysis: found: C, 64.3; H, 8.1; N, 5.9; Cl, 7.4%; $C_{25}H_{36}N_2O_4 \cdot HCl$ requires: C, 64.6; H, 8.0; N 6.0; Cl, 7.6%.

EXAMPLE 27

A solution of N-methy-N-propargyl 4-[2-(N-benzyl-N-(2-hydroxy-3phenoxypropyl)amino)ethyl]phenoxyacetamide (1.0 g) was dissolved in propan-2-ol (70 ml). 10% Palladium on carbon catalyst (0.2 g) was added and the mixture hydrogenated overnight under an atmosphere of hydrogen. The catalyst was separated by filtration through Keiselguhr and the filtrate evaporated under reduced pressure to give an oil. This residue was dissolved in dichloromethane (70 ml) and the pH (as indicated on moist test paper) was adjusted to 3 by adding a saturated solution of HCl in ether. The solvent was evaporated and this process was repeated as described in Example 26. The final residual oil (0.9 g) was suspended in a minimum amount of propan-2-ol from which it crystallised. A small amount of methyl acetate was added before the solid was filtered off and air-dried to give N-methyl-N-propargyl-4-[2-(2-hydroxy-3-phenoxypropylamino)ethyl]-phenoxyacetamide hydrochloride salt (0.3 g) mp 105°–107° C.. NMR: 0.73–0.92[m,3H, hindered rotamers CH$_2$CH$_3$]; 1.35–1.67[m,2H, hindered rotamers, NCH$_2$CH$_2$CH$_3$]; 2.80 and 2.96[pr.s,3H, hindered rotamers, N-CH$_3$]; 2.84–3.02[m,2H,CHHD 2C$_6$H$_4$]; 3.02–3.30[m,4H,CH$_2$NHCHHD 2]; 3.98[m,2H, OCH$_2$CHOH]; 4.20[m,1H,CHOH]; 4.74[s,2H,OCH$_2$CO]; 6.80–6.98[m,5H, aromatic H]; 7.10–7.34[m,4H, aromatic H].

The starting material was obtained as follows: Using a process similar to that used in Example 8 except that N-methyl-N-propargylamine was used in place of piperidine and the reaction time extended to 4 weeks at room temperature to give N-methy-N-propargyl-4-[2-(N-benzyl-N-(2-hydzoxy-3-phenoxypropyl)amino)ethyl]-phenoxyacetamide as an oil isolated by chromatography using K60 silica and eluting with an increasing gradient of 10 to 22% ethyl acetate in dichloromethane. The product was obtained as one spot material as judged by thin layer chromatography (Rf 0.35 on silica using 10% ethyl acetatedichloromethane as eluant).

EXAMPLE 28

A solution of potassium hydroxide (1.4 g) in methanol (20 ml) was added dropwise to a stirred solution of hydroxylamine hydrochloride (1.4 g) and methyl 4-[2-(2-hydroxy-3-phenoxypropylamino)ethyl]phenoxyacetate (1.8 g) in methanol at ambient temperature. The resulting suspension was stirred for 3days, and then glacial acetic acid (0.5 ml) added, and stirring continued for a further 2-hours. The solid was removed by filtration and washed with methanol (20 ml). The filtrate and washings were combined and evaporated in vacuo to yield a pasty yellow solid (2.0 g).

This was purified by column chromatography on silica gel (100 g) eluting with a dichloromethane/methanol mixture (9:1 v/v) to give a colourless foam (0.45 g). This was crystallised from propan-2-ol to give 4-[2-(2-hydroxy-3-phenoxypropylamino)ethyl]-phenoxyacetohydroxamic acid (0.25 g) as colourless crystals; m.p. 126°–128° C.; microanalysis; found: C, 62.8; H, 6.7; N, 7.5; $H_2O$, 0.4%; $C_{19}H_{24}N_2O_5$. 0.1 $H_2O$ requires: C, 63.0; H, 6.7; N, 7.7; $H_2O$, 0.5%; NMR 2.6–2.9 [complex, 6H, —CH$_2$NHCH$_2$CH$_2$Ar], 3.8–4.0 [complex, 3H, PhOCH$_2$CH—], 4.4[s,2H, ArOCH$_2$CO ], 6.8–7.3 [complex, 9H, aromatic H]: m/e 361 (M+H)+.

EXAMPLE 29

A solution of 0-allylhydroxylamine hydrochloride (7.7 g) in methanol (40 ml) was added to a stirred solution of potassium hydroxide (3.9 g) in methanol (40 ml), and stirring continued for 5 minutes. The precipitate was removed by filtration and washed well with methanol (20 ml). To the combined filtrate and washings was added methyl 4-[2-(2-hydroxy-3-phenoxypropylamino)ethyl]phenoxyacetate (3.6 g) and the resulting solution stirred at reflux for 16 hours. A further solution of 0-allylhydroxylamine in methanol (20 ml) (prepared as detailed above from 0-allylhydroxylamine hydrochloride (2.2 g) and potassium hydroxide (2.2 g)) was added to the reaction mixture and the mixture was stirred at reflux for a further 5 days. The reaction mixture was cooled to ambient temperature and glacial acetic acid (2.0 ml) was added. A small amount of solid material was removed by filtration and the filtrate evaporated to dryness in vacuo to yield a pale yellow syrup (6.0 g). This was purified by column chromatography on silica (250 g) eluting with an increasing amount of methanol in dichloromethane (7.5% v/v to 10% v/v) to yield 0-allyl-4-[2-(2-hydroxy-3phenoxypropylamino)ethyl]phenoxyacetohydroxamate (0.84 g) as the solid free base. This was dissolved in ethyl acetate/dichloromethane (100 ml 1:1 v/v) and acidified with a solution of hydrogen chloride in methylene chloride. Evaporation followed by two crystallisations from propan-2-ol yielded the corresponding hydrochloride salt (0.2 g); m.p. 146°–148° C.; NMR: 2.9–3.3 [complex, 6H, —CH$_2$NHCH$_2$CH$_2$ Ar], 4.0 [m,2H, PhOCH$_2$—], 4.25 [m,1H, CH$_2$CH(OH)CH$_2$], 4.35 (d,2H, OCH$_2$CH=CH$_2$], 4.5 [s,2H, ArO—CH$_2$CO], 5.2-5.4[dd,2H, —CH=CH$_2$], 5.95-6.05[m,1H, —CH=CH$_2$], 6.9-7.4 [complex, 9H, aromatic H]: microanalysis, found: C, 60.1; H, 6.6; N, 6.0; Cl, 8.0%, $C_{22}H_{28}N_2O_5$.HCl requires: C, 60.5; H, 6.7; N, 6.4; Cl, 8.1%; m/e 401 (MH)+.

EXAMPLE 30

To a solution of 0,N-dimethyl-4-[2-(N-benzyl-N-(2-hydroxy-3-phenoxypropyl)amino)ethyl]phenoxyacetohydroxamate (0.95g) in ethyl acetate (100 ml) was added benzyl chloride (4 drops) and 5% palladium on charcoal (0.56 g). The suspension was stirred vigorously at ambient temperature and pressure in an atmosphere of hydrogen until no starting material remained (judged by thin layer chromatography). Charcoal was added to the reaction mixture and left to stand for 0.5 hours and then the mixture was filtered through diatomaceous earth. The diatomaceous earth was washed with ethyl acetate/methanol (1:1, 100 ml) and the filtrate and washings combined and evaporated in vacuo. The resulting white solid was treated with excess hydrogen chloride in ethyl acetate/dichloromethane. The hydrochloride salt thus obtained was crystallised from acetone to give 0,N-dimethyl-4-[2-(2-hydroxy-3phenoxypropylamino)ethyl]phenoxyacetohydroxamate hydrochloride (0.25 g) as colourless crystals; m.p. 139°–141° C.; microanalysis, found: C, 59.4; H, 6.9; N, 6.5; Cl, 8.2%; $C_{21}H_{28}N_2O_5$.HCl requires: C, 59.4; H, 6.9; N, 6.6; Cl, 8.3%; NMR 2.9–3.3 [complex, 6H, CH$_2$NHCH$_2$CH$_2$-Ar]; 3.1 [s,3H, CH$_3$N—]; 3.75[s,3H, CH$_3$O—]; 4.0[m,2H, —OCHHD 2CH]; 4.3[m,1H, —CHOH—]; 4.9 [s,2H, —OCH$_2$CO ]; 6.8–7.3 [complex, 9H, aromatic H]; m/e 389 (MH)+.

The necessary benzyl-protected starting material was obtained as follows:

Sodium hydride (0.44 g of a 50% w/w dispersion in mineral oil) was added to a stirred solution of 4-[2-(N-benzyl-N-(2-hydroxy-3-phenoxypropyl)amino)ethyl]-phenoxyacetohydroxamic acid (2.0 g) in dry N,N-dimethylformamide (DMF) (50 ml), and stirring was continued until complete solution was attained (approximately 0.5 hours). Methyl iodide (0.56 ml) was then added, and the resulting solution stirred for 2 hours. The reaction mixture was poured into water (300 ml) and extracted with ethyl acetate (4×50 ml). The combined extracts were washed (water and then brine), dried (MgSO$_4$) and evaporated to yield a yellow oil (2.6 g). This was purified by column chromatography on silica (150 g) eluting with an increasing amount of ethyl acetate in dichloromethane (1:19 v/v to 1:4 v/v) to give 0,N-dimethyl-4-[2-(N-benzyl-N-(2-hydroxy-3-phenoxypropyl)amino)ethyl]phenoxyacetohydroxamate (1.05 g) as a pale yellow oil; NMR 2.6-2.9 [complex, 6H, —CH$_2$N—CH$_2$CH$_2$Ar]2.75 [s,3H, CH$_3$N—]3.75 [s,3H, CH$_3$O—], 3.8-4.1[complex, 5H, NCH$_2$Ph, PhOCH$_2$CHOH], 4.8 [s,2H, OCH$_2$C], 6.7-7.4 complex, 14H, aromatic H].

The necessary benzyl-protected hydroxamic acid starting material was obtained by reaction of methyl 4-[2-(N-benzyl-N-(2-hydroxy-3-phenoxypropyl)amino)ethyl]phenoxyacetate with hydroxylamine hydrochloride and potassium hydroxide in a manner analogous to Example 28. Thus, 4-[2-(N-benzyl-N-(2-hydroxy-3-phenoxypropyl)amino)ethyl]-phenoxyacetohydroxamic acid was obtained as a colourless solid; microanalysis, found: C, 68.7; H, 6.7; N, 5.9; H20, 1.1%; $C_{26}H_{30}N_2O_5$. 0.25 $H_2O$ requires: C, 68.6; H, 6.7;

N, 6.2; H$_2$O 1.0%; NMR 2.6-2.9 [complex, 6H, CH$_2$NCH$_2$CH$_2$Ar], 3.7-4.1 [complex, 5H, —OCH$_2$-CHOH—+NCH$_2$Ph], 4.4[s,2H, —OCH$_2$CO—], 6.8-7.4[complex, 14H, aromatic H]: m/e 451 (MH)+.

EXAMPLE 31

A solution of 0-isopropyl-4-[2-(N-benzyl-N-(2-hydroxy-3-phenoxypropyl)amino)ethyl]phenoxyacetonhydroxamate (1.1 g) in ethyl acetate (150 ml) was debenzylated in a manner analogous to Example 30. The product was isolated as the free base, reacted with hydrogen chloride and crystallised from propan-2-ol to yield 0-isopropyl-4-[2-(2-hydroxy-3-phenoxypropylamino)ethyl]phenoxyacetohydroxamate hydrochloride, (0.34 g), m.p. 168°-9° C.; microanalysis, found: C, 60.4; H, 7.1; N, 6.3; Cl, 7.9%; C$_{22}$H$_{30}$N$_2$O$_5$.HCl requires: C, 60.2; H, 7.1; N, 6.4; Cl, 8.1%; NMR 1.1-1.2 [d,6H, (CH$_3$)$_2$CH—], 2.9-3.3[complex, 6H, CH$_2$NHCH$_2$CH$_2$Ar], 3.9-4.1 [complex, 3H, PhOCH$_2$+—OCH(CH$_3$)$_2$], 4.25 [complex, 1H, PhOCH$_2$C-H(OH)—], 4.5 [s,2H, —OCH$_2$CO—], 6.9-7.4[complex, 9H, aromatic H]; m/e 403 (MH)+.

The necessary N-benzyl protected starting material was prepared in a manner analogous to Example 30. Thus, 4-[2-(N-benzyl-N-(2-hydroxy-3-phenoxypropyl)amino)ethyl]phenoxyacetohydroxamic acid (2.65 g) in dimethylformamide (DMF) (25 ml) was reacted sequentially with sodium hydride (0.28 g of a 50% w/w dispersion in mineral oil) and 2-propyl bromide (0.56 ml). Standard work-up and purification yielded 0-isopropyl-4-[2-(N-benzyl-N-(2-hydroxy-3-phenoxypropyl)amino)ethyl]phenoxyacetohydroxamate (1.1 g) as a colourless solid; NMR 1.15[d,6H,, (CH$_3$)$_2$CH—], 2.8-3.1 [complex, 6H, CH$_2$NHCH$_2$CH$_2$ Ar]; 3.8-4.2 [complex, 6H, PhOCH$_2$CH(OH)+NCH$_2$Ph+—OCH(CH$_3$)$_2$], 4.45 [s,2H, O—CH$_2$CO—], 6.8-7.5 [complex, 14H, aromatic H].

EXAMPLE 32

A solution of 0-n-butyl-4-[2-(N-benzyl-N-(2-hydroxy-3-phenoxypropyl)amino)ethyl]phenoxyacetohydroxamate (0.65 g) in ethyl acetate (130 ml) was debenzylated in a manner analogous to Example 30. The desired product was isolated as the free base, reacted with hydrogen chloride and crystallised from propan-2-ol to yield 0-n-butyl-4-[2-(2-hydroxy-3-phenoxypropylamino)ethyl]-phenoxyacetohydroxamate hydrochloride (0.13 g), m.p. 175°-177° C.; microanalysis, found: C, 60.6; H, 7.2; N, 5.8; Cl, 7.6%; C$_{23}$H$_{32}$N$_2$O$_5$.HCl requires : C, 61.0; H, 7.3; N, 6.2; Cl. 7.8%; NMR 0.9 [t,3H, CH$_3$CH$_2$—], 1.3-1.6[complex, 4H, CH$_3$CH$_2$CH$_2$CH$_2$], 2.9-3.3 [complex, 6H, CH$_2$NCH$_2$Ar], 3.8 [t,2H, —OCH$_2$of n-butyl], 4.0 [m,2H, PhOCH$_2$—], 4.5 [m,1H, CH—OH], 4.5 [s,2H, O—CH$_2$CO—], 6.9-7.4-[complex, 9H, aromatic H]; m/e 417 (MH)+.

The necessary N-benzyl protected starting material was obtained in a manner analogous to Example 30. Thus, 4-[2-(N-benzyl-N-(2-hydroxy-3-phenoxypropyl)amino)ethyl]phenoxyacetohydroxamic acid (1.2 g) in DMF (25 ml) was reacted sequentially with sodium hydride (0.14 g of a 50% w/w dispersion in mineral oil) and n-butyl bromide (0.3 ml). Standard work-up and purification yielded 0-n-butyl-4-[2-(N-benzyl-N-(2-hydroxy-3-phenoxypropyl)amino)ethyl]phenoxyacetohydroxamate (0.65 g) as a colourless solid; NMR 0.9 [t,3H, CH$_3$ of n-butyl]. 1.3-1.6 [complex, 4H, CH$_3$CH$_2$CH$_2$CH$_2$], 2.7-3.0 [complex, 6H, CH$_2$NCH$_2$CH$_2$Ar], 3.8-4.1 [complex, 7H, PhOCH$_2$CH(OH) +—OCHhd 2 of n-butyl+N—CH$_2$Ph], 4.5 [s,2H, OCH$_2$CO—], 6.8-7.5 [complex, 14H, aromatic H]; m/e 507 (MH)+.

EXAMPLE 33

0-Benzyl-4-[2-(2-hydroxy-3-phenoxypropylamino)-ethyl]phenoxyacetohydroxamate

In a similar manner to Example 29 using O-benzylhydroxylamine hydrochloride as starting material, O-benzyl-4-[2-(2-hydroxy-3-phenoxypropylamino)ethyl]-phenoxyacetohydroxamate hydrochloride was obtained as colourless crystals, mp 162°-4° C.; microanalysis, found: C, 63.8; H, 6.3; N, 5.6%; C26H30N2O5.HCl requires C, 64.1; H, 6.4; N,5.7%; NMR 2.85-3.35 [m,6H, CH$_2$NCH$_2$CH$_2$Ar], 4.00 [m,2H, —OCH$_2$], 4.25 [m,1H, CHOH], 4.5[s,2H, —NOCH$_2$]4.86[s,2H, OCH$_2$CO]and 6.8-7.5[m,14H, Ar]; m/e 451(MH+).

EXAMPLE 34

To a solution of N-(4-[2-(N-benzyl-N-(2-hydroxy-3-phenoxypropyl)amino)ethyl]phenoxyacetyl)isooxazolidine (2.4 g) in ethyl acetate (250 ml) was added 10% palladium on charcoal (0.4 g). The suspension was stirred vigorously at ambient temperature and pressure in an atmosphere of hydrogen until no starting material remained (by thin layer chromatography) (2 days). The reaction mixture was diluted with dichloromethane (40 ml), treated with charcoal for 15 minutes and filtered through diatomaceous earth, washing with ethyl acetate/dichloromethane (1:1, 200 ml) and the filtrate and washing were combined and evaporated in vacuo. The resulting residue was treated with hydrogen chloride in dichloromethane solution. The hydrochloride salt thus obtained was crystallised from ethanol to give N-(4-[2-(2-hydroxy-3-phenoxypropylamino)ethyl]phenoxyacetyl)isooxazolidine as colourless prisms m.p. 144°-6°; microanalysis, found: C, 60.8; H, 6.7; N, 6.4; Cl, 8.3%; C$_{22}$H$_{28}$N$_2$O$_5$.HCl requires C, 60.5; H, 6.7; N, 6.4; Cl, 8.1%; NMR 2.28[quintet, 2H, —CH$_2$CH$_2$CH$_2$—], 2.85-3.25 [m,6H, CH$_2$NCH$_2$CH$_2$Ar], 3.63[t,2H, ONCH$_2$], 4.02 [m,4H, NOCH$_2$ and OCH$_2$], 4.26[m,1H, CHOH], 4.83[s,2H, OCH$_2$CO]and 6.8-7.4[m,9H, Ar]; m/e 401 (MH+).

The necessary benzyl protected starting material was prepared as follows:

Sodium hydride (0.6 g of a 50% w/w dispension in mineral oil) was added to a stirred solution of 4-[2-(N-benzyl-N-(2-hydroxy-3-phenoxypropyl)amino)ethyl]-phenol (3.77 g) in dry N,N-dimethylformamide (DMF) (40 ml) and stirring was continued until complete solution was attained (approximately 1 hour). N-Chloroacetyl isooxazolidine (1.5 g) was then added as a solution in N,N-dimethylformamide (5 ml) and the resulting solution stirred for 3hours. The reaction mixture was poured into water and extracted with ethyl acetate ($\times$3). The combined extracts were washed (water ($\times$2) and then brine), dried (MgSO$_4$) and evaporated to yield a pale golden oil (4.7 g). This was purified by column chromatography on silica gel eluting with ethyl acetate to give N-(4-[2-(N-benzyl-N-(2-hydroxy-3-phenoxypropyl)-amino)ethyl]phenoxyacetyl)isooxazolidine as a colourless oil; NMR 2.27 [quintet, 2H, —CH$_2$CH$_2$CH$_2$—], 2.8-3.2[m,6H, CH$_2$NCH$_2$CH$_2$Ar], 3.62[t,2H, O—NCH$_2$], 3.8-4.1[m,4H, NOCH$_2$ and OCH$_2$], 4.22[m,3H, NCHPh and CHOH], 4.78[s,2H, OCH$_2$CO] and 6.7-7.6[m,14H, Ar]. (M+H)+ was observed in the chemical ionisation induced mass spectrum at m/e 491 [C$_{29}$H$_{34}$H$_2$O$_5$ requires M+ at 490].

N-Chloroacetyl isooxazolidine was prepared as follows:

To a stirred slurry of finely powdered isooxazolidine hydrochloride (H. King, J. Chem. Soc. 433,1942) (11.0 g) in dry ether (200 ml) at 0° C. was added triethylamine (28.0 ml) and a solution of chloroacetyl chloride (8.0 ml) in ether (50 ml). The reaction mixture was stirred for a further 4 hours, whilst the temperature rose to room temperature. The precipitate triethylamine hydrochloride was filtered off through diatomaceous earth and the filter bed washed well with ether. The combined ether solutions were evaporated to give N-chloroacetyl isooxazolidine as an oil (11.5 g) NMR (CDCl$_3$) 2.38[quintet, 2H, CH$_2$], 3.78[t,2H, NCH$_2$], 4.05[t,2H, OCH$_2$] and 4.22 [s,2H, ClCH$_2$CO].

EXAMPLE 35

In a similar manner to that described in Example 34 but using N-chloroacetyl tetrahydroisooxazine as starting material, N-(4-2-(2-hydroxy-3-phenoxypropylamino)ethyl]phenoxyacetyl) tetrahydroisooxazine was obtained as colourless crystals mp 128°–134° C.; microanalysis, found: C, 61.5; H, 6.9; N, 6.1; Cl, 8.2%; C$_{23}$H$_{30}$N$_2$O$_5$. HCl requires C, 61.3; H,6.9, N,6.2; Cl, 7.9%, NMR 1.6–1.9 [m,4H, CH$_2$CH$_2$CH$_2$CH$_2$], 2.85–3.25[m,6H, CH$_2$NCH$_2$CH$_2$Ar], 3.68[t,2H, ONCH$_2$]4.02[m,4H, NOCH$_2$and OCH$_2$], 4.27[m,1H, CHOH]4.84[s,2H, OCH$_2$CO]and 6.8–7.4[m,9H, ArH]; m/e 415 (MH$^{30}$).

The necessary starting-material, N-chloroacetyl tetrahydroisooxazine, was prepared from tetrahydroisooxazine hydrochloride (H. King., J. Chem. Soc., 433, 1942) in a manner similar to that described in Example 34, and was obtained as an oil, NMR (CDCl$_3$) 1.80[m,4H, —CH$_2$CH$_2$—], 3.75[t,2H, NCH$_2$], 3.98[m,2H, OCH$_2$] and 4.15[s,2H, ClCH$_2$CO].

EXAMPLE 36

As stated previously, suitable pharmaceutical compositions of compounds of formula I defined hereinbefore may be obtained by standard formulation techniques.

A typical tablet formulation suitable for oral administration to warm-blooded animals comprises as active ingredient a micronised and/or milled form of a compound of formula I, or a pharmaceutically acceptable salt thereof, as defined hereinbefore (for example as described in one of the preceding Examples), and may be produced by direct compression or wet granulation followed by compression together with micronised and/or milled lactose containing a standard disintegrant and/or lubricant.

We claim
1. A compound of the formula (I):

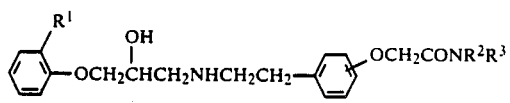

wherein:
R$^1$ is hydrogen; fluoro or chloro;
R$^2$ is hydrogen; C$_{1-6}$ alkyl; C$_{1-6}$ alkyl substituted by a group selected from hydroxy, C$_{1-4}$ alkoxy, phenoxy, carbamoyl, C$_{1-6}$ alkylcarbamoyl, di-C$_{1-6}$ alkylcarbamoyl, phenyl and chlorophenyl; C$_{3-6}$ alkenyl; C$_{3-6}$ alkenyl substituted by a group selected from hydroxy, C$_{1-4}$ alkoxy, phenoxy, carbamoyl, C$_{1-6}$ alkylcarbamoyl, di-C$_{1-6}$ alkylcarbamoyl, phenyl and chlorophenyl; C$_{3-6}$ alkynyl; C$_{3-5}$ cycloalkyl; phenyl or phenyl substituted by a radical selected from halo, C$_{1-4}$ alkyl, C$_{1-4}$ alkoxy, trifluoromethyl, cyano and nitro;
R$^3$ is hydrogen; C$_{1-6}$ alkyl; or is a group —OR$^4$ wherein R$^4$ is hydrogen; C$_{1-6}$ alkyl; C$_{1-6}$ alkyl substituted by hydroxy; C$_{1-6}$ alkyl substituted by C$_{1-4}$ alkoxy; C$_{3-6}$ alkenyl; C$_{3-6}$ alkenyl substituted by hydroxy; C$_{3-6}$ alkenyl substituted by C$_{1-4}$ alkoxy; or R$^4$ is C$_{3-6}$ alkynyl, phenyl, naphthyl, phenyl C$_{1-4}$ alkyl or naphthyl C$_{1-4}$ alkyl;
or a pharmaceutically acceptable salt thereof.

2. A compound according to claim 1 wherein R$^2$ is C$_{1-6}$ alkyl; C$_{1-6}$ alkyl substituted by a group selected from hydroxy, C$_{1-4}$ alkoxy and phenyl; C$_{3-6}$ alkenyl; or C$_{3-6}$ alkenyl substituted by a group selected from hydroxy, C$_{1-4}$ alkoxy and phenyl.

3. A compound according to claim 1 wherein R$^1$ is hydrogen.

4. A compound according to claim 1 wherein the phenoxypropylaminoethyl group and the OCH$_2$CONR$^2$R$^3$ substituent are in para-relationship.

5. A compound according to claim 1 wherein R$^3$ is hydrogen or C$_{1-6}$ alkyl.

6. A compound according to claim 1 wherein R$^3$ is hydroxy or C$_{1-6}$ alkoxy.

7. A compound according to claim 1 which is:
N-2-methoxyethyl 4-[2-(2-hydroxy-3-phenoxypropylamino)-ethyl]phenoxyacetamide,
N-3-methoxypropyl 4-[2-(2-hydroxy-3-phenoxypropylamino)-ethyl]phenoxyacetamide,
N-3-methoxypropyl 4-[2-(2S-hydroxy-3-phenoxypropylamino)-ethyl]phenoxyacetamide,
N-2-ethoxypropyl 4-[2-(2-hydroxy-3-phenoxypropylamino)-ethyl]phenoxyacetamide,
or a pharmaceutically acceptable salt thereof.

8. A compound according to claim 1 which is:
N,N-diethyl 4-[2-(2-hydroxy-3-phenoxypropylamino)ethyl]-phenoxyacetamide,
N-ethyl-N-methyl 4-[2-(2-hydroxy-3-phenoxypropylamino)-ethyl]phenoxyacetamide,
4-[2-(2-hydroxy-3-phenoxypropylamino)ethyl]-phenoxyacetohydroxamic acid,
or a pharmaceutically acceptable salt thereof.

9. A compound according to claim 1 in laevorotatory optically active form.

10. A pharmaceutical composition which comprises a compound according to claim 1 or a pharmaceutically acceptable salt thereof and a pharmaceutically acceptable carrier.

11. A pharmaceutical composition according to claim 10 characterised in that it is of the sustained release type.

12. A compound of the formula (IX):

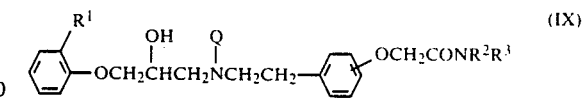

wherein:
R$^1$ is hydrogen; fluoro or chloro;
R$^2$ is hydrogen; C$_{1-6}$ alkyl; C$_{1-6}$ alkyl substituted by a group selected from hydroxy, C$_{1-4}$ alkoxy, phenoxy, carbamoyl, C$_{1-6}$ alkylcarbamoyl, di-C$_{1-6}$ alkylcarbamoyl, phenyl and chlorophenyl; C$_{3-6}$ alkenyl; C$_{3-6}$ alkenyl substituted by a group selected from hydroxy, $C_{1-4}$ alkoxy, phenoxy, carbamoyl, $C_{1-6}$ alkylcarbamoyl, di-$C_{1-6}$alkylcarbamoyl, phenyl and chlorophenyl; $C_{3-6}$ alkynyl; $C_{3-5}$ cycloalkyl; phenyl or phenyl substituted by a radical selected from halo, $C_{1-4}$ alkyl, $C_{1-4}$ *alkoxy, trifluoromethyl, cyano and nitro*;

$R^3$ is hydrogen; $C_{1-6}$ alkyl; or is a group —$OR^4$ wherein $R^4$ is hydrogen; $C_{1-6}$ alkyl; $C_{1-6}$ alkyl substituted by hydroxy; $C_{1-6}$ alkyl substituted by $C_{1-4}$ alkoxy; $C_{3-6}$ alkenyl; $C_{3-6}$ alkenyl substituted by hydroxy; $C_{3-6}$ alkenyl substituted by $C_{1-4}$ alkoxy; or $R^4$ is $C_{3-6}$ alkynyl, phenyl, naphthyl, phenyl $C_{1-4}$ alkyl or naphthyl $C_{1-4}$ alkyl; and Q is benzyl, 4-methoxybenzyl or 3,4-dimethoxybenzyl.

* * * * *